United States Patent
Chen et al.

(10) Patent No.: US 9,970,852 B2
(45) Date of Patent: May 15, 2018

(54) MEASURING TENSILE STRENGTH OF TIGHT ROCK USING ELECTROMAGNETIC HEATING

(71) Applicant: Aramco Services Company, Houston, TX (US)

(72) Inventors: JinHong Chen, Katy, TX (US); Daniel Georgi, Houston, TX (US); Lorne Davis, Seguin, TX (US); Hui-Hai Liu, Katy, TX (US)

(73) Assignee: SAUDI ARABIAN OIL COMPANY (SA)

(*) Notice: Subject to any disclaimer, the term of this patent is extended or adjusted under 35 U.S.C. 154(b) by 128 days.

(21) Appl. No.: 14/920,273

(22) Filed: Oct. 22, 2015

(65) Prior Publication Data

US 2016/0116388 A1  Apr. 28, 2016

Related U.S. Application Data

(60) Provisional application No. 62/067,616, filed on Oct. 23, 2014.

(51) Int. Cl.
*G01N 3/60* (2006.01)
*G01N 33/24* (2006.01)
*G01N 3/18* (2006.01)

(52) U.S. Cl.
CPC ............... *G01N 3/60* (2013.01); *G01N 3/18* (2013.01); *G01N 33/24* (2013.01); *G01N 33/246* (2013.01); *G01N 2203/0057* (2013.01)

(58) Field of Classification Search
CPC ............ G01N 3/60; G01N 3/18; G01N 33/24; G01N 33/246; G01N 2203/0057

(Continued)

(56) References Cited

U.S. PATENT DOCUMENTS

| 5,226,310 A | 7/1993 | Steiger |
| 8,446,156 B2 | 5/2013 | Morrison |

(Continued)

FOREIGN PATENT DOCUMENTS

| CN | 203785967 U | 8/2014 | |
| RU | 2261327 C1 * | 9/2005 | |
| WO | WO 2011112294 A1 * | 9/2011 | ............. G01N 33/24 |

OTHER PUBLICATIONS

Translation RU 2261327 C1 Sep. 29, 2005.*

(Continued)

*Primary Examiner* — Natalie Huls
*Assistant Examiner* — Monica S Young
(74) *Attorney, Agent, or Firm* — Bracewell LLP; Constance Gall Rhebergen

(57) ABSTRACT

A method for determining the tensile strength of a rock sample comprising the steps of obtaining the rock sample, measuring a water content of the rock sample through a water measurement method, determining a matrix bulk modulus of the rock sample, wherein the matrix bulk modulus is determined through a matrix modulus method, heating the rock sample with electromagnetic energy such that the electromagnetic energy heats the water content in the rock sample from an initial temperature, wherein heating the water content causes a pore-water pressure of the rock sample to increase, detecting a break in the rock sample with a sensor, wherein the increase in the pore-water pressure causes the rock sample to break, wherein the break occurs at a break time, at a break temperature; and calculating the pore-water pressure through the water content, the matrix bulk modulus, and the break temperature of the water content.

16 Claims, 4 Drawing Sheets

(58) Field of Classification Search
USPC .......................................................... 73/37
See application file for complete search history.

(56) References Cited

U.S. PATENT DOCUMENTS

| | | | |
|---|---|---|---|
| 8,701,760 B2 | 4/2014 | Parsche | |
| 2009/0321132 A1* | 12/2009 | Ouellet | E21B 7/15 175/11 |
| 2013/0013209 A1* | 1/2013 | Zhu | G01N 33/24 702/6 |
| 2014/0041940 A1 | 2/2014 | Shnell | |

OTHER PUBLICATIONS

PCT International Search Report and The Written Opinion of the International Searching Authority dated Jan. 29, 2016; International Application No. PCT/US2015/057097; International Filing Date: Oct. 23, 2015.

Tavallali, A., et al.; Effect of Layer Orientation on the Failure of Layered Sandstone Under Brazilian Test Conditions; International Journal of Rock Mechanics & Mining Sciences; Jan. 25, 2010; pp. 313-322; vol. 47, No. 2; Elsevier, Ltd.

Wang, X-Q., et al.; Physical Properties and Brittle Strength of Thermally Cracked Granite Under Confinement; Journal of Geophysical Research: Solid Earth; Dec. 26, 2013; pp. 6099-6112; vol. 118, No. 12; American Geophysical Union.

Wei, C.K., et al.; Heat and Mass Transfer in Water-Laden Sandstone: Microwave Heating; AICHE Journal, May 1985; pp. 842-848; vol. 31, No. 5.

R. Meisels et al., "Microwave propagation and absorption and its thermo-mechanical consequences in heterogeneous rocks," International Journal of Mineral Processing 135 (2015), pp. 40-51.

\* cited by examiner

MEASURING TENSILE STRENGTH OF TIGHT ROCK USING ELECTROMAGNETIC HEATING

TECHNICAL FIELD OF THE INVENTION

The present invention relates to a method for determining the tensile strength of materials. More specifically, the present invention relates to methods for determining the tensile strength of tight rock and tight materials using electromagnetic heating.

BACKGROUND OF THE INVENTION

Tensile strength of reservoir rock is one of the most important factors in designing hydraulic fracturing for reservoirs comprising sedimentary rocks. This includes tight shale gas reservoirs, tight sedimentary sandstone and chalk reservoirs. Tensile strength is also important in the determination of wellbore stability of wells drilled in sedimentary rocks. Tensile strength is one of the determinant parameters for the pumping rate of aqueous fluids in hydraulic fracturing and for using an appropriate mud weight in drilling. Mechanical tests on natural rock samples involve large instruments and complex procedures, in part, because significant force is required to break the rock. In addition, the laboratory mechanical tests require special sample preparation and the results are often unreliable, preventing measurement of tensile strength at the wellsite.

Traditional mechanical force testing methods use external force to measure tensile strength and include Brazilian Test methods and pull methods. The Brazilian Test method involves an indirect measurement of the tensile strength by compressing the unconfined rock. Pull tests require specific sample shapes and misalignment in setting up the sample produces incorrect results. In the Brazilian Test, there is a risk of producing tensile failure at the ends by subjecting the specimens to compressive force along their length until the flat ends split.

Therefore, a method that provides direct reliable measurement of material tensile strength with less equipment is desired.

SUMMARY OF THE INVENTION

The present invention relates to a method for determining the tensile strength of rock. More specifically, the present invention relates to methods for determining the tensile strength of tight rock using electromagnetic heating.

In one aspect of the present invention, a method for determining the tensile strength of a rock sample is provided. The method includes the steps of obtaining the rock sample, measuring a water content of the rock sample, wherein the water content is measured through a water measurement method, determining a matrix bulk modulus of the rock sample, wherein the matrix bulk modulus is determined through a matrix modulus method, heating the rock sample with electromagnetic energy such that the electromagnetic energy heats the water content in the rock sample from an initial temperature, wherein heating the water content causes a pore-water pressure of the rock sample to increase, detecting a break in the rock sample with a sensor, wherein the increase in the pore-water pressure causes the rock sample to break, wherein the break occurs at a break time, wherein the break occurs at a break temperature, determining the break temperature, and calculating the pore-water pressure at the break time from the water content, the matrix bulk modulus, and the break temperature of the water content, wherein the tensile strength of the rock sample is the pore-water pressure at which the break occurs.

In certain embodiments of the present invention, the rock sample is selected from the group consisting of shale, tight shale, tight organic-rich shale, sandstone, tight sandstone, carbonate rock, tight carbonate rock, and cement. In certain embodiments of the present invention, the water measurement method is selected from the group consisting of NMR measurement, dielectric measurement, a gravimetric method, Dean-Stark analysis, and combinations thereof. In certain embodiments of the present invention, the matrix modulus method is selected from the group consisting of experimental methods, estimation methods based on the individual component, and combinations thereof. In certain embodiments of the present invention, the sensor is selected from the group consisting of acoustic sensors, temperature sensors, and strain gauges. In certain embodiments of the present invention, the rock sample is subjected to a confining stress. In certain embodiments of the present invention, the electromagnetic energy is produced by an electromagnetic wave source. In certain embodiments of the present invention, the electromagnetic wave source is a microwave. In certain embodiments of the present invention, the electromagnetic wave source has a frequency between 1 and 50 GHz. In certain embodiments of the present invention, the rock sample is saturated with saturation water, the saturation water operable to increase the water content of the rock sample. In certain embodiments of the present invention, the saturation water comprises a doping agent, the doping agent operable to increase the absorption of electromagnetic radiation by the rock sample.

In a second aspect of the present invention, a method for determining the tensile strength of a rock sample is provided. The method includes the steps of obtaining the rock sample, heating the rock sample with electromagnetic energy such that the electromagnetic energy heats a water content in the rock sample from an initial temperature, wherein heating the water content causes a temperature-dependent pressure in the rock sample to increase, detecting a break in the rock sample with a sensor, wherein the increase in the temperature-dependent pressure causes the rock sample to break, wherein the break occurs at a break time, wherein the break occurs at a break temperature, determining the break temperature, and calculating the temperature-dependent pressure at the break time, wherein the temperature-dependent pressure is calculated based on a difference between the break temperature and the initial temperature of the rock sample, wherein the tensile strength of the rock sample is the temperature-dependent pressure at which the break occurs.

In certain embodiments of the present invention, the rock sample is selected from the group consisting of shale, tight shale, tight organic-rich shale, sandstone, tight sandstone, carbonate rock, tight carbonate rock, and cement. In certain embodiments of the present invention, the difference between the break temperature and the initial temperature of the rock sample is calculated based on the temperature change of a water content of the rock sample, wherein the water content is measured through a water measurement method. In certain embodiments of the present invention, the water measurement method is selected from the group consisting of NMR measurement, dielectric measurement, a gravimetric method, Dean-Stark analysis, and combinations thereof. In certain embodiments of the present invention, the temperature-dependent pressure is modified based on determining a matrix bulk modulus of the rock sample, wherein the matrix bulk modulus is determined through a matrix modulus method. In certain embodiments of the present invention, the matrix modulus method is selected from the group consisting of experimental methods, estimation methods based on the individual component, and combinations thereof. In certain embodiments of the present invention, the sensor is selected from the group consisting of acoustic sensors, temperature sensors, and strain gauges. In certain embodiments of the present invention, the rock sample is subjected to a confining stress. In certain embodiments of the present invention, the electromagnetic energy is produced by an electromagnetic wave source. In certain embodiments of the present invention, the electromagnetic wave source is a microwave. In certain embodiments of the present invention, the electromagnetic wave source has a frequency between 1 and 50 GHz. In certain embodiments of the present invention, the rock sample is saturated with saturation water, the saturation water operable to increase the water content of the rock sample. In certain embodiments of the present invention, the saturation water comprises a doping agent, the doping agent operable to increase the absorption of electromagnetic radiation by the rock sample.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION

Figure 1:
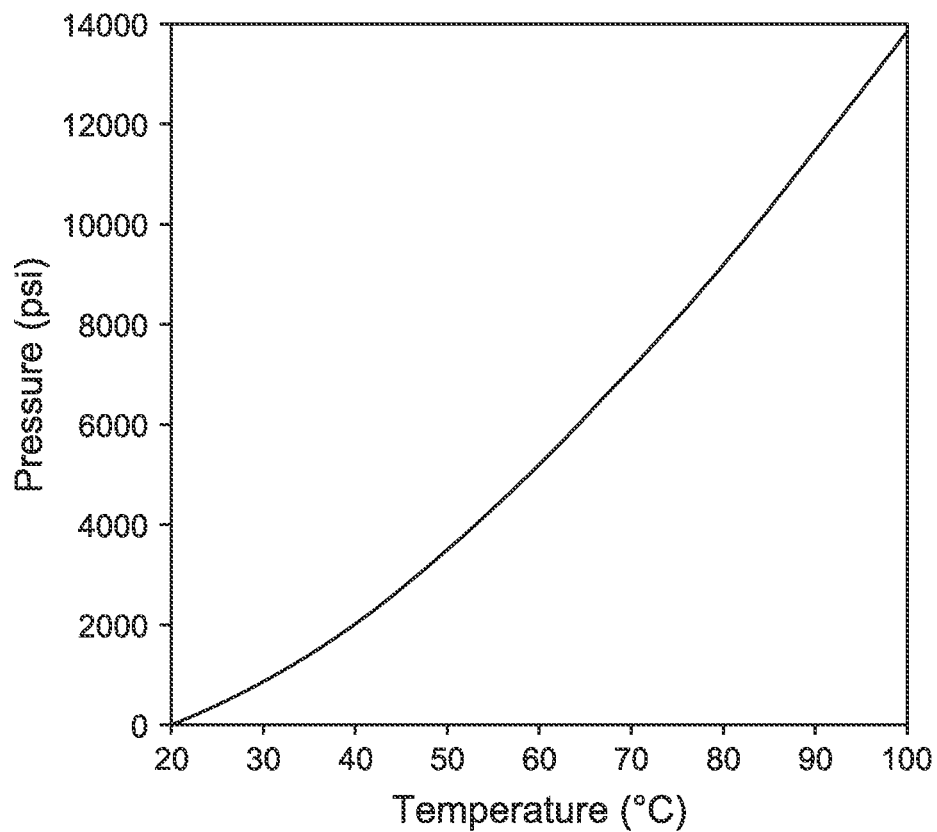
FIG. 1 is a graph of the temperature-dependent pore-water pressure for water in a rock at initial conditions of 1 atm and 20° C.

While the invention will be described in connection with several embodiments, it will be understood that it is not intended to limit the invention to those embodiments. On the contrary, it is intended to cover all the alternatives, modifications and equivalence as may be included within the spirit and scope of the invention defined by the appended claims.

In one embodiment, a method for determining the tensile strength of a rock sample is provided. The method for determining the tensile strength of the rock sample uses electromagnetic heating to rapidly increase the temperature of the water content of the rock sample. The water content is the water confined in the pores of the rock matrix of the rock sample. The increase in the temperature of the water content causes an increase in the pore-water pressure of the rock sample, which eventually causes the rock sample to break or fail. The methods of the present invention determine the pore-water pressure at which the rock sample breaks, and thus, the tensile strength of the rock sample. The method establishes a quantitative relationship between the temperature of the water content and the pore-water pressure that can be used to measure the tensile strength of the rock sample.

When water is heated, the temperature increase can cause changes to the pressure of the water, the volume of the water, or both. When water confined in low permeability rocks is heated the volume changes or pressure changes are constrained by the surrounding rock matrix. As a result, changes to the equilibrium state of water due to the elevated temperature is a balance between the rock matrix and the confined water.

Equation of State for Water

The pressure increase attributed to heating the water content in the rock sample can be obtained from an equation of state (EOS). Any EOS for water can be used, one of skill in the art will appreciate that an accurate EOS is desired. In at least one embodiment of the present invention, the EOS for water is expressed as follows:

$$z = \frac{p_w V_w}{RT_w} \qquad \text{equation (1)}$$

where R is the specific gas constant of water in kJ/(kgK), $T_w$ is the temperature of the water in K, $p_w$ is pressure in MPa, and $V_w$ is the volume of water in m³. In at least one embodiment of the present invention, the EOS can be rewritten with the molar density according to the following equation:

$$z = \frac{p_w}{RT_w \rho_w} \qquad \text{equation (2)}$$

where $\rho_w$ is the molar density of water in kg/m³. In at least one embodiment of the present invention, the use of equation (1) and equation (2) requires experimental data covering potential pressure and temperature ranges. In at least one embodiment of the present invention, a computer program contains the experimental data for a range of temperatures and pressures. In at least one embodiment of the present invention, a computer program can be loaded with experimental data developed by the International Association for the Properties of Water and Steam (IAPWS) covering the density of water at temperatures in the range from 0° C. to 800° C. at pressures less than or equal to 100 MPa and temperatures in the range of 800° C. to 2000° C. at pressures less than or equal to 50 MPa.

Without being bound to a particular theory, it is believed that the EOS of water in small pores can deviate from the above equation, the deviation can be experimentally determined, and the deviation can have minimal effect on the outcome. In at least one embodiment of the present invention, the method of determining the tensile strength of the rock sample uses the EOS in equation (2) in the absence of any deviations due to water in small pores.

Pressure Change and Density Change Models

As noted above, the temperature increase of the water content can cause a change in pressure, a change in volume (or density), or changes to both the pressure and the volume of the water content in the rock matrix. In certain embodiments of the present invention, pressure is determined based on a model that assumes no volume change (or density change) of the water content. In certain embodiments of the present invention, pressure is determined based on a model that assumes a change in volume of the water content.

1. No Change in Volume Model of Pressure Determination

In at least one embodiment of the present invention, the rock matrix of the rock sample is incompressible, such that the volume (or density) of the water content does not change with an increase in the temperature of the water content; the net result of the increase of the temperature of the water content is to elevate the pressure of the water content to a temperature-dependent pressure. In such embodiments, the temperature-dependent pressure can be determined from the EOS. In at least one embodiment, the temperature-dependent pressure can be determined from the EOS and a computer program.

Referring to FIG. 1, an embodiment of the present invention of the calculated temperature-dependent pressure determined from the EOS in equation (2) is shown, with initial conditions of water at 1 atm (14.7 psi or 0.101325 MPa) and 20° C. According to the embodiment shown in FIG. 1, the results are in the absence of the effects due to leak off of vapor and volume changes (density changes) of the water due to expansion in the pores. In at least one embodiment of the present invention, the tensile strength of shale rock is about 1,000 psi (6.89 MPa). From FIG. 1, it can be seen that the temperature-dependent pressure reaches this value when the temperature increases by about 10° C.

2. Density Change Model

Figure 2:
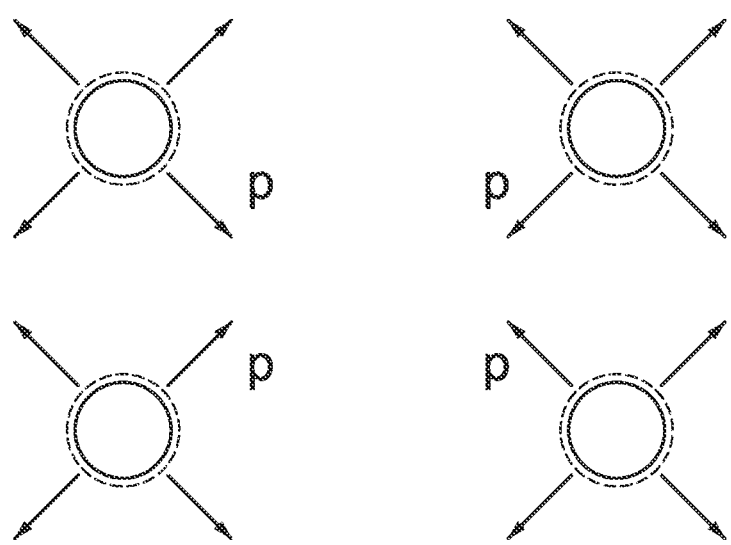
FIG. 2 is a representation of the compression on the rock matrix due to the elevated pore-water pressure of the water in the pores of the rock sample.

In certain embodiments of the present invention, the increased pressure of the water content due to the increased temperature can apply sufficient pressure on the rock sample to compress the rock matrix allowing the water content to expand. In at least one embodiment of the present invention, the expansion of the water content can slow down the rate of pressure change in the rock sample, as compared to when no volume change is observed. Referring to FIG. 2, an illustration of how the elevated pore-water pressure due to water in multiple pores compresses the rock matrix of the rock sample is shown.

The increased pore-water pressure (increase in pressure of the water content) due to the increase in temperature of the water content and the change in density (volume) of the water content can be calculated according to the following equation:

$$p_w^t = p_w^0 + \frac{K_m x_w}{(1 - x_w)}\left(\frac{\rho_w^0}{\rho_w^t} - 1\right) \quad \text{equation (3)}$$

where the superscripts t and 0 indicate points of time, $K_m$ is the matrix bulk modulus in GPa, $x_w$ is the water content, which is the volume fraction of water to the total rock volume and $p_w$ and $\rho_w$ are as defined with respect to equations (1) and (2). Equation (3) is derived based on the following assumptions: the volume change of the rock matrix due to compression by the water content is assumed to be equal to the volume change due to the expansion of the water content and the total volume of the rock is assumed to experience minimal to no significant volume change. Equation (3) further assumes that the pressure exerted on the rock matrix equals the pore pressure exerted by the water content. The volume change of the rock matrix is a function of the matrix bulk modulus and the initial volume of the rock matrix. Water content is defined as the volume fraction of water to the volume of total rock, including water in pores as well as water in shale interlayers and may not be equal to the water saturation in the "conventional" pore space.

Thus, equation (3) shows that the pore-water pressure of the heated water content depends on the rock sample matrix bulk modulus, water density, and water content. As the water density is a function of temperature and pore-water pressure according to equation (2), combining equations (2) and (3) provides the pore-water pressure at a given temperature when the matrix bulk modulus and water content are known.

Figure 3A:
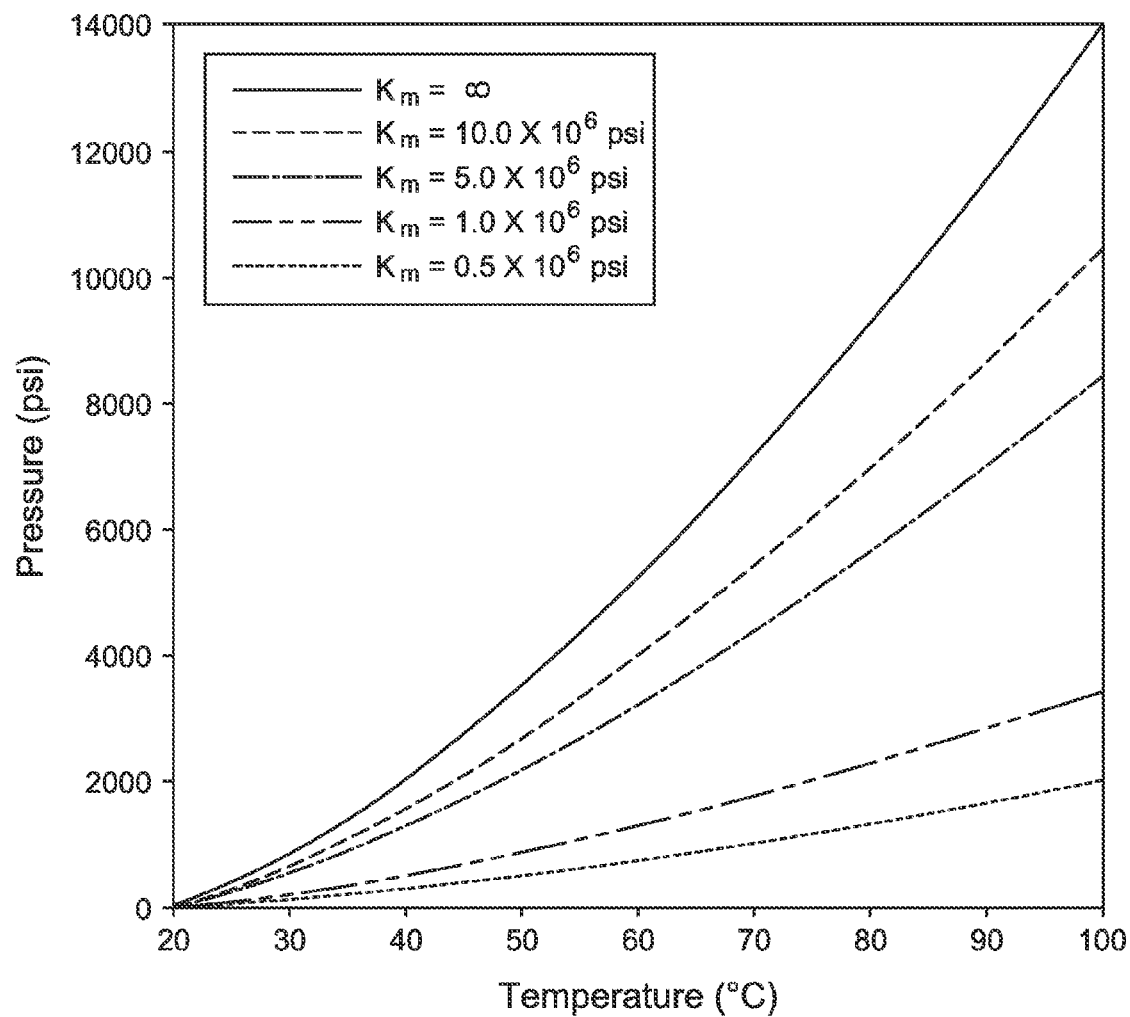
FIG. 3a is a graph of pore-water pressure change as a function of temperature for different matrix bulk moduli for rock samples with 10% water content at initial conditions of 1 atm and 20° C.

Referring to FIG. 3a, the pore-water pressure change for different bulk moduli with 10% water content at initial conditions of 1 atm and 20° C. is shown. FIG. 3a shows that the rate of pore-water pressure change depends on the rock's matrix bulk modulus. Without being bound to a particular theory, it appears that smaller bulk moduli allow the volume of the water content, and thereby the density, to increase, and as a result, the pore-water pressure change is moderated.

Figure 3B:
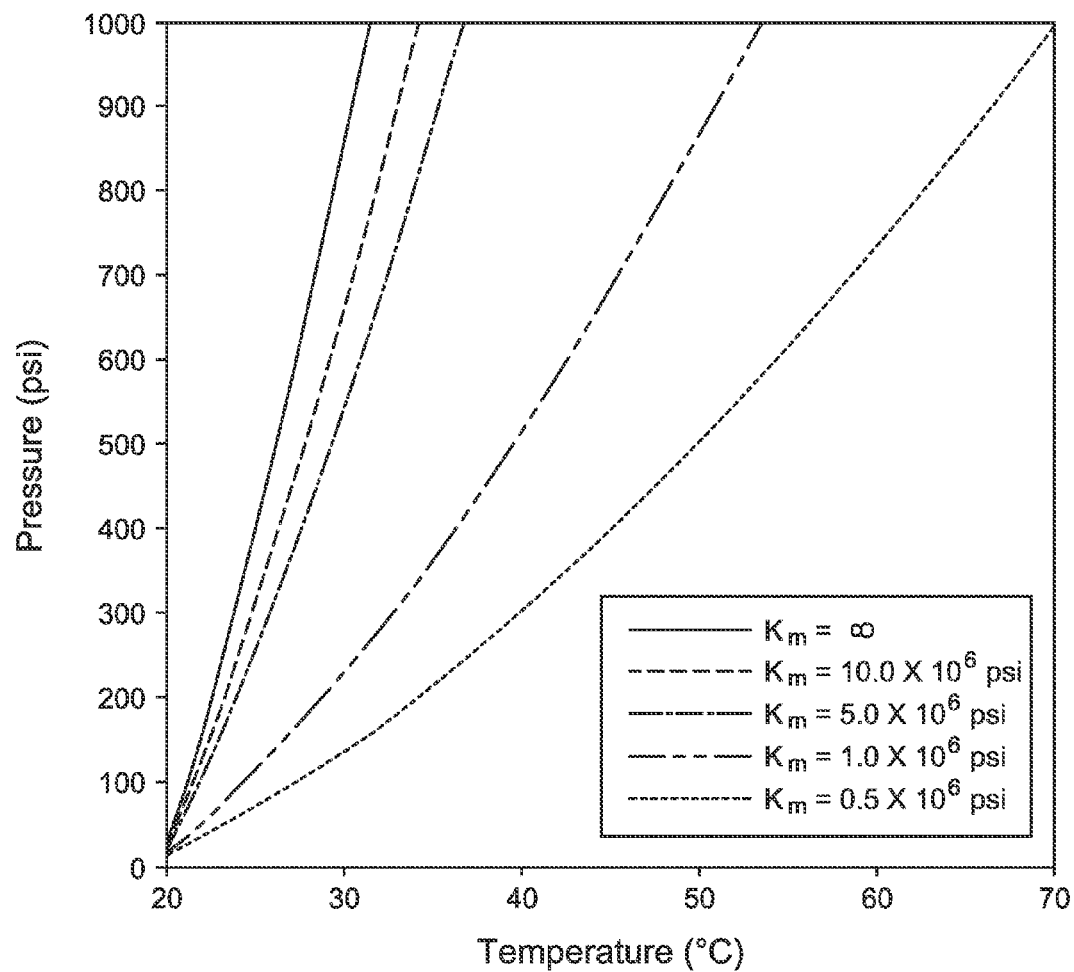
FIG. 3b is the same data shown in FIG. 3a with a smaller scale on the pressure axis.

Referring to FIG. 3b, an enlarged section of FIG. 3a corresponding to the range of pressures expected to break rock samples according to the method of the present invention is shown.

Figure 4:
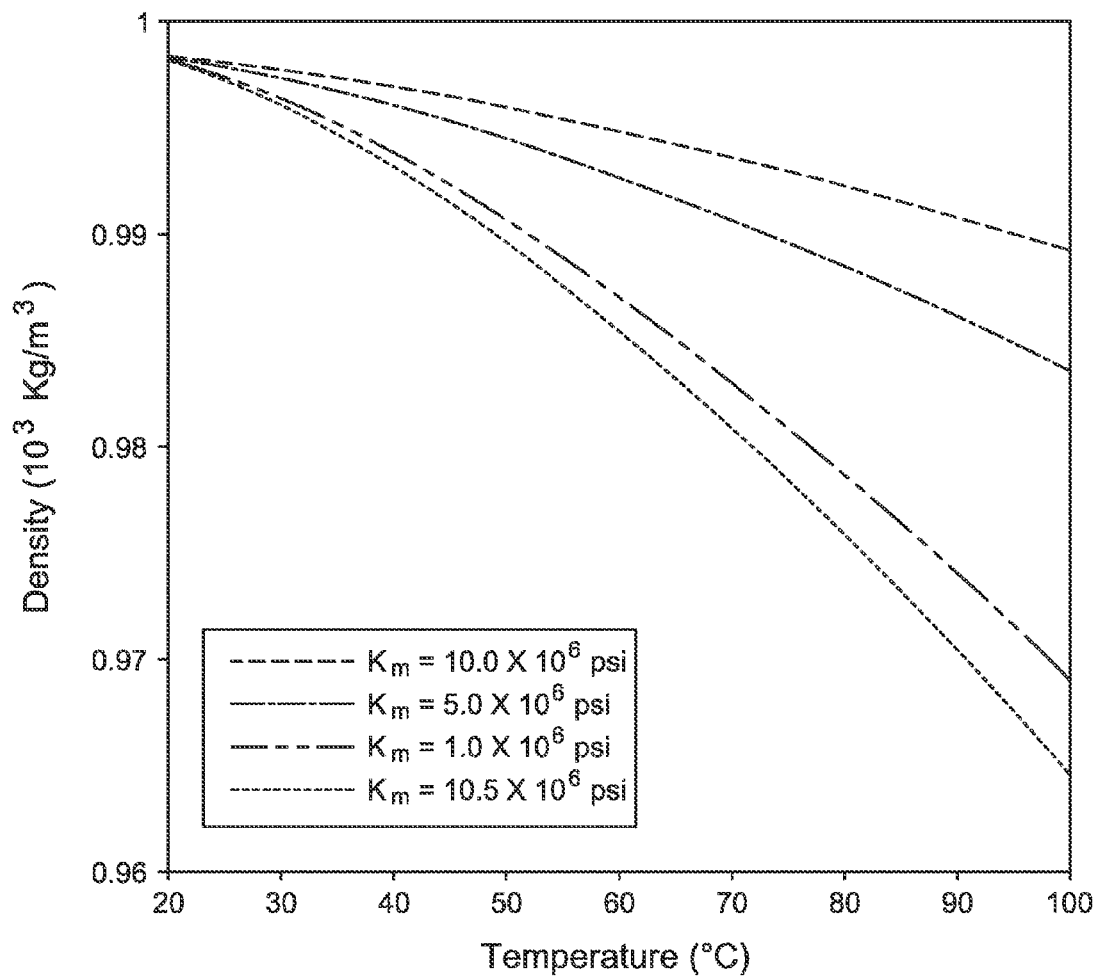
FIG. 4 is a graph of density change as function of temperature different matrix bulk moduli for rock samples with 10% water content at initial conditions of 1 atm and 20° C.

Referring to FIG. 4, a graph of the density change of the water content in the pores versus temperature is shown. A 4% change in the water density results in about a 0.4% change in the rock matrix volume, when the water content volume is 10% of the rock volume.

Embodiments of the method of the present invention can be performed using any rock samples where the structure of the rock sample is provided by a rock matrix that encloses void spaces, where water or other fluid in the void spaces has a higher expansion coefficient than the surrounding rock matrix of the rock sample. Any tight material can be tested using the present invention. Embodiments of the method of the present invention can be performed using any rock sample containing connate water for which a tensile strength is desired to be determined. The rock samples can be naturally occurring rock samples or man-made rock samples. In at least one embodiment of the present invention, the rock sample is anisotropic. In at least one embodiment of the present invention, the rock sample is homogenous. Examples of naturally occurring rock samples include shale, tight shale, tight organic-rich shale, sandstone, tight sandstone, carbonate rock, and tight carbonate rock. Naturally occurring rock samples can be obtained from outcrops, subsurface core samples, or cuttings of any arbitrary shape. Examples of man-made rock samples include cement. In one embodiment of the invention, the method is performed on a Portland cement. Man-made rock samples can be obtained from cuttings, molds, or other methods capable of shaping a man-made rock. In at least one embodiment of the present invention, the shape of the rock sample does not impact the tensile strength measurement. In at least one embodiment of the present invention, the rock sample has a low permeability. In at least one embodiment of the present invention, the rock sample has a high permeability. In at least one embodiment of the present invention, the water content of the rock sample can be increased by saturating the rock sample with saturation water or exposing the rock sample to water vapor. In at least one embodiment of the present invention, the saturation water used to saturate the rock sample can include a doping agent. The doping agent can increase the absorption of electromagnetic radiation in the water content. Without being bound to a particular theory, a doping agent can influence the rate of temperature increase, without impacting the tensile strength. In other words, a doping agent allows the determination of tensile strength in a shorter time without impacting the final value. In at least one embodiment of the present invention, the saturation water used to saturate the rock sample can be treated to increase its viscosity. Without being bound to a particular theory, increasing the viscosity of the water in the pores decreases the mobility of the water from the pores, decreasing the mobility reduces the pressure bleeds-off (water leak off) and thereby increases measurement accuracy. In at least one embodiment of the present invention, increasing the viscosity of the water in the pores improves the accuracy of the method to measure tensile strength for permeable rock samples. In at least one embodiment of the present invention, the saturation water can include a doping agent and the rock sample can be treated to increase its viscosity. In at least one embodiment of the present invention, the rock sample can be coated with a seal to prevent pressure from escaping the rock sample prior to the rock breaking.

In embodiments of the present invention, the rock sample can be sized so that the electric field of the electromagnetic wave source is known, or can be characterized, inside the rock sample. In at least one embodiment of the present invention, the rock sample can be sized so that the electric field produced by the electromagnetic wave source is uniform or substantially uniform inside the rock sample. In at least one embodiment, the electric field is approximately uniform. The shape of the rock sample does not impact the uniformity of the electric field in the rock sample. A uniform electric field is produced by sizing the rock sample to be smaller than the electromagnetic power penetration depth extends through the entire rock sample, according to the following equation:

$$D = \frac{\lambda}{2\pi} \{2\varepsilon'[1+(\varepsilon''/\varepsilon')^2]^{1/2} - 1\}^{-1/2} \qquad \text{equation (4)}$$

where $\lambda$ is the wavelength of the electromagnetic wave source in free space and $\varepsilon''$ and $\varepsilon'$ are the dielectric loss and dielectric constant, respectively.

In a step of the method for determining the tensile strength of a rock sample, the water content of the rock sample is measured. The water content is measured using a water measurement method. Any water measurement method capable of determining the amount of water confined in the rock sample can be used. Examples of water measurement methods include NMR measurement, dielectric measurement, a gravimetric method, Dean-Stark analysis, and combinations thereof. In certain embodiments, where NMR measurement or dielectric spectroscopy are to be used as the water measurement method, the water measurement method is performed prior to the step of heating using electromagnetic energy. In certain embodiments of the present invention, the gravimetric method includes measurement of water collected and/or weight loss of the rock sample during a drying procedure after the electromagnetic heating step of the tensile strength step. Twinned samples can be used for determining the water content of the rock sample. "Twinned samples", as used herein, refers to the use of two rock samples taken from the same source, identical in size and shape, and without observable fractures. In at least one embodiment of the present invention, twinned samples can be used due to loss of fluid from the original sample during the step of heating with electromagnetic energy, the loss of fluid affects the measured water content if measured after the heating step.

In a step of the method for determining the tensile strength of a rock sample, the matrix bulk modulus of the rock sample is determined. The matrix bulk modulus is determined based on the mineral composition of the rock sample using a matrix modulus method. Any matrix modulus method capable of determining the matrix bulk modulus can be used. Examples of matrix modulus methods include experimental methods, estimation methods based on the individual component, and combinations thereof. Estimation methods based on the individual component include the Reuss approach and the Voigt approach. The equations for the Reuss approach and the Voigt approach are shown below, where $x^i$ represents the volume fraction and $K_m^i$ represents the bulk modulus of the $i^{th}$ component of the matrix, respectively.

$$K_m^{Reuss} = \left(\sum_i \frac{x^i}{K_m^i}\right)^{-1} \qquad \text{equation (5a)}$$

$$K_m^{Voigt} = \left(\sum_i x^i K_m^i\right)^{-1} \qquad \text{equation (5b)}$$

The volume fraction, $x^i$, of each matrix component can be calculated from mineralogical characterization of the rock sample. Known matrix bulk moduli of materials that can commonly be found in reservoir rocks include quartz between about 36-38 GPa, calcite between about 63-77 GPa, and kerogen between about 3.5-5 GPa. Without being bound to a particular theory, $K_m^{Reuss}$ and $K_m^{Voigt}$ represent the lower and upper limit of the matrix bulk moduli, respectively.

In at least one embodiment of the present invention, the matrix bulk modulus is determined using a matrix modulus method that takes an average of the $K_m^{Reuss}$ and $K_m^{Voigt}$ according to the following equation:

$$K_m = (K_m^{Reuss} + K_m^{Voigt})/2 \qquad \text{equation (6)}$$

In at least one embodiment of the present invention, the grain shape or the pore shape can be considered in determining the matrix bulk modulus, which can increase the accuracy of $K_m$. The matrix bulk modulus is determined based on the entire rock sample. In a preferred embodiment of the present invention, the matrix bulk modulus is determined prior to the step of heating the rock sample with electromagnetic heating. In at least one embodiment of the present invention, the matrix bulk modulus is determined before the water content of the rock sample is measured.

Heating of the rock sample is due to an electromagnetic wave source that produces electromagnetic energy. Any electromagnetic wave source capable of producing electromagnetic energy can be used. The electromagnetic wave source produces electromagnetic energy in the range between about 1 kHz and about 300 GHz, alternately between about 300 MHz and about 300 GHz, alternately between about 1 GHz and about 100 GHz, and alternately between about 1 GHz and about 50 GHz. In at least one embodiment of the present invention, the electromagnetic wave source is a microwave that produces microwave energy. Microwave energy, in the form of microwave radiation, heats materials with non-negligible dielectric losses. Dielectric losses quantify a dielectric material's inherent dissipation of electromagnetic energy. In at least one embodiment of the present invention, the rock sample is placed in a microwave. In at least one embodiment of the present invention, the electromagnetic wave source can heat the water content and, thus, increase the temperature of the water content without increasing the temperature of rock grains in the rock sample. In at least one embodiment of the present invention, the electromagnetic wave source emits a single frequency in the absence of a function that automatically adjusts power output. Using an electromagnetic wave source with a single frequency and constant power output means that the power output by the electromagnetic wave source is constant and the heat generated in the rock sample for a given size and shape depends only on the dielectric loss of the water content. In at least one embodiment of the present invention, the electromagnetic wave source includes a waveguide.

In the method for determining the tensile strength of a rock sample, an elapsed time is measured. The elapsed time is the total time the electromagnetic source produces electromagnetic energy. An initial time, the time of turning on the electromagnetic wave source so that it produces electromagnetic energy, is measured and recorded at or just prior to the initial time. In at least one embodiment of the present invention, the initial time can be noted as time 0. The initial temperature of the rock sample is recorded. The electromagnetic energy heats the water content in the rock sample causing an increase in the temperature of the water content in the rock sample. The electromagnetic energy continues to heat the water content in the rock sample until a sensor detects a break in the rock sample. The sensor can be any sensor capable of detecting a break in the rock sample. As used herein, "break" includes the plural breaks, such that the sensor detects that the rock has broken, not the quantity of breaks, and as such the sensor can detect one or more than one break. Examples of sensors include acoustic sensors, temperature sensors and strain gauges. In at least one embodiment of the present invention, the sensor is integrated with the electromagnetic wave source. In at least one embodiment of the present invention, the sensor is separate from the electromagnetic wave source.

The break time, the time at which the break occurred, is recorded. The break time is the time at which the water content reaches the break temperature causing the rock sample to break. The break time can be less than 60 minutes, alternately less than 50 minutes, alternately less than 40 minutes, alternately less than 30 minutes, alternately less than 20 minutes, alternately less than 10 minutes, alternately less than 5 minutes, alternately less than 1 minute. In at least one embodiment of the present invention, the electromagnetic wave source is set to heat the water content at a rate such that the break time occurs according to the following condition:

$$\frac{\tau_t}{\tau_p} < \sim 0.1 \qquad \text{equation (7)}$$

where $\tau_t$ is the break time and $\tau_p$ is the characteristic time for pressure diffusion. In at least one embodiment of the present invention, where the rock sample has a high permeability, the electromagnetic wave source is designed to achieve the condition of equation (7). In certain embodiments and without being bound to a particular theory, pressure diffusion can be disregarded in certain embodiments of the present invention when water pressure does not have sufficient time to diffuse within the rock sample.

The elapsed time is calculated as the difference between the break time and the initial time.

When the break in the rock sample occurs, the electromagnetic wave source is turned to the off position, such that electromagnetic energy is no longer produced. In at least one embodiment of the present invention, the electromagnetic wave source senses the break and automatically turns to the off position. In at least one embodiment of the present invention, the electromagnetic wave source is manually turned to the off position.

In a step of the method for measuring the tensile strength of a rock sample, the break temperature is determined. The break temperature is the temperature of the water content at which the break occurred. Any method of determining the break temperature can be used. In at least one embodiment of the present invention, the break temperature is determined by direct measurement. Direct measurement can be accomplished through the use of infrared sensors, fiber optic sensors, or any other sensor known in the art. In at least one embodiment of the present invention, the break temperature is determined by determining the total heat absorbed by the water content. Examples of methods for determining the total heat absorbed by the water content include estimation based on the power output of the electromagnetic wave source and experimentation using a control water sample.

Estimation of Total Heat Based on the Power Output of the Electromagnetic Wave Source In at least one embodiment of the present invention, the total heat absorbed by the water content can be estimated based on the measured or calculated power output of the electromagnetic wave source, according to the following equations:

$$P_{av} = \frac{1}{2}\omega\varepsilon'' \int_V E \cdot E^* \cdot dV \qquad \text{equation (8)}$$

$$\varepsilon^* = \varepsilon' + i\varepsilon'' \qquad \text{equation (9)}$$

where $P_{av}$ is the average power produced by the electromagnetic wave source, $\omega$ is the electromagnetic wave frequency, E is the electric field strength and E * is the conjugate of electric strength. The electric field strength and electromagnetic wave frequency are constants for a specific electromagnetic wavelength. The complex dielectric constant, $\in^*$, is based on the dielectric constant, $\in'$ and dielectric loss, $\in''$.

The total heat Q adsorbed by the sample is then an integration of the average power obtained in Eq. (8) over time from initial time to the break time.

The dielectric constant and dielectric loss of water are temperature dependent, according to the following equations:

$$\in' = 85.215 - 0.33583T \qquad \text{equation (10)}$$

$$\in'' = 320.658T^{-1.0268} \qquad \text{equation (11)}$$

In at least one embodiment of the present invention, the dielectric constant, $\in'$, assumes only the absolute values ignoring the anisotropic nature of the constant.

Experimentation to Determine Total Heat Absorbed by the Water Content.

In some embodiments of the present invention, a control water sample that matches the size, salinity, and amount of water as the water content in the rock sample can be created to determine total amount of heat absorbed. An initial temperature is measured. The control water sample is placed in the electromagnetic wave source and electromagnetic energy is applied for a time equal to the elapsed time. The change in the temperature of the control water sample after the electromagnetic energy is applied for the length of time from time 0 to the break time is measured.

In at least one embodiment, the amount of heat absorbed by the control water sample can be determined according to the following equation:

$$Q_{water} = m_{water} \int_{T^0}^{T^t} C_w \, dT \qquad \text{equation (12)}$$

where $C_w$ is the temperature dependent isochoric heat capacity and $m_{water}$ is the mass of the control water sample. In at least one embodiment of the present invention, a computer program for water EOS can be used to determine $C_w$. Equation (12) is then a function of the elapsed time the electromagnetic wave source is turned to the on position and allows the measurement of the heat generated in the control water sample.

Temperature change due to heating can be determined based on the following equation:

$$dT = \frac{dQ}{C_w(T)m_w + C_m m_m} \qquad \text{equation (13)}$$

where dQ is the heat needed to cause a temperature change; dT is the change in water temperature; $C_w$ is the water specific heat; $m_w$ is the water mass; $C_m$ is the specific heat of the rock matrix, and $m_m$ is the mass of the rock matrix. Integrating equation (12) provides an equation where temperature is dependent on the total heat absorbed by the water content is as follows:

$$T_t = T_0 + \int_0^{Q_{rock}} \frac{dQ}{C_w(T)m_w + C_m m_m} \qquad \text{equation (14)}$$

The dielectric loss of the control water, $\epsilon_{water}$ and the entire rock sample, $\epsilon_{rock}$ can be measured. Without being bound to a particular theory, it is believed, that the dielectric loss of the entire rock sample is mainly due to the trapped water, thus, the contribution of the rock matrix to the dielectric loss is negligible. $Q_{rock}$ is the total heat absorbed by the rock sample from the electromagnetic wave source and can be equated to the total heat absorbed by the water content in the rock sample according to the following equation:

$$Q_{rock}(t) = Q_{water}(t) \frac{S^*_{rock}}{S^*_{water}} \qquad \text{equation (15)}$$

Thus, equations (14) and (15) can be used to determine break temperature. In at least one embodiment of the present invention, the break temperature, water content, and matrix bulk modulus can be used with equations (5) and (6) to determine the pore-water pressure of the rock matrix at the break time. The pore-water pressure of the rock matrix at the break time is the tensile strength.

In certain embodiments of the present invention, the tensile strength of the rock sample is determined in the absence of an external force being applied. In at least one embodiment of the present invention, the tensile strength of the rock sample is directly determined.

The present invention advantageously allows a method to measure the tensile strength of a reservoir rock that more closely approximates the hydraulic fracturing process, by using fluid pressure in the pores to break the reservoir rock, thus providing for more accurate and reliable measurements for design hydraulic fracturing processes.

In at least one embodiment of the present invention, electromagnetic wave energy pulverizes the rock sample, by heating the water within. In at least one embodiment, the method to measure the tensile strength is in the absence of measuring the temperature gradient between different minerals in the rock sample. The method to determine the tensile strength of a rock sample by increasing the temperature of water content within the pores of the rock sample uses less energy than a method to increase the temperature of minerals within the rock sample.

The method to determine the tensile strength of a rock sample is in the absence of producing steam within the rock sample. Without being bound to a particular theory, the pressure within the pores is high enough to suppress steam formation.

In at least one embodiment of the present invention, the rock sample is subjected to a confining stress. In at least one embodiment of the present invention, the confining stress is a vice. In at least one embodiment of the present invention, the confining stress is a clamp.

The method for measuring the tensile strength of a rock sample is suitable for determining the tensile strength of cement to be used in construction. The method for measuring the tensile strength is useful for measuring the tensile strength of cements due to the many water filled pores in cement, despite having low permeability (on the order of nano Darcy to pico Darcy).

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed.

We claim:

1. A method for determining the tensile strength of a rock sample, the method comprising the steps of:
    obtaining the rock sample;
    measuring a water content of the rock sample, wherein the water content is measured through a water measurement method, wherein the water measurement method is selected from the group consisting of NMR measurement, dielectric measurement, a gravimetric method, Dean-Stark analysis, and combinations thereof;
    determining a matrix bulk modulus of the rock sample, wherein the matrix bulk modulus is determined through a matrix modulus method, wherein the matrix modulus method is selected from the group consisting of experimental methods, estimation methods based on individual components, and combinations thereof;
    heating the rock sample with electromagnetic energy such that the electromagnetic energy heats the water content in the rock sample from an initial temperature, wherein heating the water content causes a pore-water pressure of the rock sample to increase, wherein the electromagnetic energy is produced by an electromagnetic wave source, wherein the electromagnetic wave source produces electromagnetic energy in the range between 1 kHz and 300 GHz;

detecting a break in the rock sample with a sensor while heating the rock sample with the electromagnetic energy, wherein the increase in the pore-water pressure causes the rock sample to break,
wherein the break occurs at a break time,
wherein the break occurs at a break temperature;

determining the break temperature; and calculating the pore-water pressure at the break time from the water content, the matrix bulk modulus, and the break temperature of the water content, wherein the tensile strength of the rock sample is the pore-water pressure at which the break occurs.

2. The method of claim 1, wherein the rock sample is selected from the group consisting of shale, tight shale, tight organic-rich shale, sandstone, tight sandstone, carbonate rock, tight carbonate rock, and cement.

3. The method of claim 1, wherein the sensor is selected from the group consisting of acoustic sensors, temperature sensors, and strain gauges.

4. The method of claim 1, wherein the rock sample is subjected to a confining stress, wherein the confining stress is selected from the group consisting of a vice and a clamp.

5. The method of claim 1, wherein the electromagnetic wave source produces electromagnetic energy in the range between 1 GHz and 50 GHz.

6. The method of claim 1, wherein the rock sample is saturated with saturation water, the saturation water operable to increase the water content of the rock sample.

7. The method of claim 1, wherein the estimation method based on the individual component is selected from the group consisting of a Reuss approach and a Voigt approach.

8. A method for determining the tensile strength of a rock sample, the method comprising the steps of:
obtaining the rock sample;
heating the rock sample with electromagnetic energy such that the electromagnetic energy heats a water content in the rock sample from an initial temperature, wherein heating the water content causes a temperature-dependent pressure in the rock sample to increase, wherein the electromagnetic energy is produced by an electromagnetic wave source, wherein the electromagnetic wave source produces electromagnetic energy in the range between 1 kHz and 300 GHz;
detecting a break in the rock sample with a sensor while heating the rock sample with the electromagnetic energy, wherein the increase in the temperature-dependent pressure causes the rock sample to break,
wherein the break occurs at a break time,
wherein the break occurs at a break temperature;
determining the break temperature; and
calculating the temperature-dependent pressure at the break time, wherein the temperature-dependent pressure is calculated based on a difference between the break temperature and the initial temperature of the rock sample, wherein the tensile strength of the rock sample is the temperature-dependent pressure at which the break occurs.

9. The method of claim 8, wherein the rock sample is selected from the group consisting of shale, tight shale, tight organic-rich shale, sandstone, tight sandstone, carbonate rock, tight carbonate rock, and cement.

10. The method of claim 8, wherein the difference between the break temperature and the initial temperature of the rock sample is calculated based on the temperature change of a water content of the rock sample, wherein the water content is measured through a water measurement method, wherein the water measurement method is selected from the group consisting of NMR measurement, dielectric measurement, a gravimetric method, Dean-Stark analysis, and combinations thereof.

11. The method of claim 8, wherein the temperature-dependent pressure is modified based on determining a matrix bulk modulus of the rock sample, wherein the matrix bulk modulus is determined through a matrix modulus method, wherein the matrix modulus method is selected from the group consisting of experimental methods, estimation methods based on individual components, and combinations thereof.

12. The method of claim 11, wherein the estimation method based on the individual component is selected from the group consisting of a Reuss approach and a Voigt approach.

13. The method of claim 8, wherein the sensor is selected from the group consisting of acoustic sensors, temperature sensors, and strain gauges.

14. The method of claim 8, wherein the rock sample is subjected to a confining stress, wherein the confining stress is selected from the group consisting of a vice and a clamp.

15. The method of claim 8, wherein the electromagnetic wave source produces electromagnetic energy in the range between 1 GHz and 50 GHz.

16. The method of claim 8, wherein the rock sample is saturated with saturation water, the saturation water operable to increase the water content of the rock sample.

* * * * *